United States Patent [19]

Forney et al.

[11] Patent Number: 5,084,086
[45] Date of Patent: Jan. 28, 1992

[54] HERBICIDE UTILITY ON RESISTANT CROPS

[75] Inventors: David R. Forney, Winterset, Iowa; Stephen K. Gee, Wilmington, Del.; James D. Long, Elkton, Md.; Matthew F. Schlecht, Newark, Del.

[73] Assignee: E. I. Du Pont de Nemours and Company, Wilmington, Del.

[21] Appl. No.: 684,408

[22] Filed: Apr. 12, 1991

[51] Int. Cl.$^5$ .................. C07D 239/42; C07D 239/69; C07D 251/42; A01N 43/66
[52] U.S. Cl. ........................................... 71/93; 71/92; 544/321; 544/332; 544/211
[58] Field of Search ...................... 71/93, 92; 544/321, 544/332, 211

[56] References Cited

U.S. PATENT DOCUMENTS 4,723,990 1/1987 Farnham .................................. 71/93

Primary Examiner—John M. Ford

[57] ABSTRACT

This invention relates to sulfonylurea herbicides which control the growth of undesired vegetation and are safe to cotton or soybean plants that contain at least one gene that confers resistance to inhibitors of acetolactate synthase, agriculturally suitable compositions thereof and a method of their use.

34 Claims, No Drawings

HERBICIDE UTILITY ON RESISTANT CROPS

BACKGROUND OF THE INVENTION

This invention relates to sulfonylurea herbicides which control the growth of undesired vegetation and are safe to cotton or soybean plants that contain at least one gene that confers resistance to inhibitors of acetolactate synthase, agriculturally suitable compositions thereof and a method of their use.

New compounds effective for controlling the growth of undesired vegetation are in constant demand not only for the control of all plant growth but also for controlling said growth while not injuring useful crops.

The "sulfonylurea" herbicides are an extremely potent class of herbicides discovered within the last several years which generally consist of a sulfonylurea bridge, —$SO_2NHCONH$—, linking two aromatic or heteroaromatic rings.

U.S. Pat. No. 4,723,990 discloses compounds of the formula

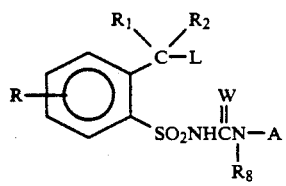

wherein:
L is, among others, Cl, F, Br;
R is H, F, Cl, Br, $NO_2$, $CF_3$, $C_1$-$C_3$ alkyl or $C_1$-$C_3$ alkoxy;
$R_1$ is H, F, Cl or $C_1$-$C_4$ alkyl;
$R_2$ is H or $CH_3$;
$R_8$ is H, $CH_3$ or $OCH_3$;
A is, among others,

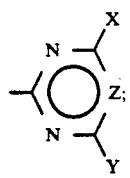

W is O or S;
X is H, Cl, Br, $CH_3$, $CH_2CH_3$, $C_1$-$C_3$ alkoxy, $CF_3$, $SCH_3$ or $CH_2OCH_3$;
Y is $CH_3$ or $OCH_3$; and
Z is N, CH, CCl, CBr, CCN, $CCH_3$, $CCH_2CH_3$, $CCH_2CH_2Cl$ or $CCH_2CH=CH_2$;
and their agriculturally suitable salts; provided that:
(1) when $R_1$ is Cl, then L is Cl or Br and $R_2$ is H;
(2) when $R_3$ is $OCH_3$, then $R_4$ is $CH_3$;
(3) when W is S, then $R_8$ is H; and
(4) when L is F, then $R_1$ is H, F, or $C_1$-$C_4$ alkyl.

SA 84/2245 discloses compounds of the formula

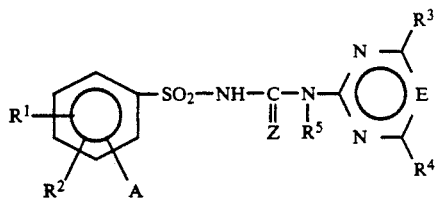

wherein:
A is $C_1$-$C_6$ haloalkyl;
$R^1$ is hydrogen, halogen, nitro, cyano, $C_1$-$C_4$ alkyl, $C_1$-$C_4$ haloalkyl, $C_1$-$C_4$ alkoxy, $C_1$-$C_4$ alkylthio, $C_1$-$C_4$ alkylsulfinyl, $C_1$-$C_4$ alkylsulfonyl, —CO—$R^6$, —$NR^7R^8$, —CO—$NR^9R^{10}$ or —$SO_2$—$NR^{11}R^{12}$;
$R^2$ is hydrogen, halogen, $C_1$-$C_4$ alkyl, $C_1$-$C_4$ alkoxy, $C_1$-$C_4$ alkylthio, $C_1$-$C_4$ alkylsulfinyl or $C_1$-$C_4$ alkylsulfonyl;
$R^3$ and $R^4$ independently of one another are each hydrogen, halogen, $C_1$-$C_4$ alkyl, $C_1$-$C_4$ haloalkyl, $C_2$-$C_4$ haloalkoxy, $C_1$-$C_4$ alkylthio, $C_1$-$C_4$ haloalkylthio, $C_2$-$C_4$ alkoxyalkyl, $C_1$-$C_4$ alkoxy or —$NR^{12}R^{13}$;
$R^5$ is hydrogen, $C_1$-$C_4$ alkyl or $C_1$-$C_4$ alkoxy;
$R^6$ is $C_1$-$C_4$ alkoxy, $C_1$-$C_4$ haloalkoxy, $C_1$-$C_4$ alkylthio, $C_2$-$C_6$ alkoxyalkoxy, hydrogen, $C_1$-$C_4$ alkyl or $C_1$-$C_4$ haloalkyl;
$R^7$, $R^8$, $R^9$, $R^{10}$, $R^{11}$, $R^{12}$ and $R^{13}$ independently of one another are each hydrogen or $C_1$-$C_4$ alkyl;
E is nitrogen or the methine bridge; and
Z is oxygen or sulfur;
and the invention relates also to the salts of these compounds, with the proviso that A is not trifluoromethyl or the group —$CR^aR^bR^c$, where $R^a$ is hydrogen, chlorine or $C_1$-$C_4$ alkyl, $R^b$ is hydrogen or methyl, and $R^c$ is chlorine or bromine.

U.S. Pat. No. 4,394,506 and U.S. Pat. No. 4,592,978 disclose compounds of the formula

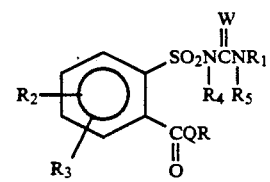

wherein:
Q is, among other, O;
R is among others, $C_1$-$C_{12}$ alkyl;
$R_2$ is H, Cl, Br, F, $C_1$-$C_3$ alkyl, —$NO_2$, —$SO_2CH_3$, —$OCH_3$, —$SCH_3$, —$CF_3$, —$N(CH_3)_2$, —$NH_2$, or —CN; and
$R_3$ is H, Cl, Br, F or $CH_3$.

U.S. Pat. No. 4,478,635 discloses compounds of the formula

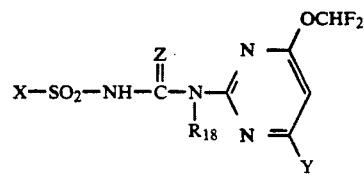

wherein:
$R_{18}$ is hydrogen, alkyl or alkoxy;

X is an unsubstituted or substituted phenyl or naphthyl radical;
Y is $C_1$–$C_3$ alkyl, $C_1$–$C_3$ haloalkyl, $C_1$–$C_3$ alkoxy, $C_1$–$C_3$ haloalkoxy, $C_1$–$C_3$ alkylthio, $C_2$–$C_3$ alkoxyalkyl, halogen or an unsubstituted amino group; and
Z is oxygen or sulfur.

None of the compounds of the instant invention are specifically disclosed in any of the above references nor do the references teach the possible use of these compounds on herbicide-resistant crops. However, compounds of the present invention are within the generic scope of the claims of the above patents.

EP-A-154,204 discloses plants, plant tissues and plant seeds, particularly corn (*Zea mays* L.), which are resistant to herbicides (including sulfonylureas) which normally inhibit the growth and development of those plants, plant tissues and plant seeds.

Sebastian et al. (Crop Science 1989 29:1403–1408) describe the selection, characterization and utility of soybean mutants which are resistant to sulfonylurea herbicides. Line W20 is specifically described.

EP-A-257,993 describes nucleic acid fragments useful in the production of transgenic plants on which the compounds and methods of the instant invention are used.

SUMMARY OF THE INVENTION

This invention relates to compounds selected from the group consisting of:
2-chloro-6-(1-fluoroethyl)-N-[[(4-methoxy-6-methyl-1,3,5-triazin-2-yl)-amino]carbonyl]benzenesulfonamide,
1-methylethyl 3-chloro-2-[[[[(4,6-dimethyl-2-pyrimidinyl)amino]carbonyl]amino]sulfonyl]benzoate, and their agriculturally suitable salts.

Specifically preferred for reasons of ease of synthesis, greater herbicidal activity, greater crop safety or optimal soil residual characteristics is a compound which is 2-chloro-6-(1-fluoroethyl)-N-[[(4-methoxy-6-methyl-1,3,5-triazin-2-yl)amino]carbonyl]benzenesulfonamide.

This invention also relates to agriculturally suitable compositions for controlling the growth of undesired vegetation containing a compound of the invention.

This invention also relates to a method for controlling the growth of undesired vegetation which comprises applying to cotton or soybean plants containing at least one gene that confers resistance to inhibitors of acetolactate synthase a compound which is selected from the group consisting of:
2-chloro-6-(1-fluoroethyl)-N-[[(4-methoxy-6-methyl-1,3,5-triazin-2-yl)amino]carbonyl]benzenesulfonamide,
1-methylethyl 3-chloro-2-[[[[(4,6-dimethyl-2-pyrimidinyl)amino]-carbonyl]amino]sulfonyl]benzoate, and
methyl 2-[[[[[4,6-bis(difluoromethoxy)-2-pyrimidinyl]amino]carbonyl]-amino]sulfonyl]benzoate.

The Preferred methods of the invention are:

1. A method as outlined above wherein the compound is selected from the group consisting of 2-chloro-6-(1-fluoroethyl)-N-[[(4-methoxy-6-methyl-1,3,5-triazin-2-yl)amino]carbonyl]benzenesulfonamide and methyl 2-[[[[[4,6-bis(difluoromethoxy)-2-pyrimidinyl]-amino]carbonyl]amino]sulfonyl]benzoate.

2. A method according to Preferred 1 wherein the compound is 2-chloro-6-(1-fluoroethyl)-N-[[(4-methoxy-6-methyl-1,3,5-triazin-2-yl)amino]carbonyl]-benzenesulfonamide.

3. A method according to Preferred 1 wherein the compound is methyl 2-[[[[[4,6-bis(difluoromethoxy)-2-pyrimidinyl]amino]carbonyl]amino]sulfonyl]benzoate.

4. A method according to any above method wherein the plant is soybean.

5. A method according to any above method wherein the plant is cotton.

6. A method according to Preferred 4 wherein the soybean plant contains the Als1 gene.

7. A method according to Preferred 6 wherein the soybean plant is selected from the group consisting of lines W20 and W4—4 or derivatives thereof.

8. A method according to Preferred 7 wherein the soybean is W20.

9. A method according to Preferred 7 wherein the soybean is W4—4.

10. A method according to Preferred 7 wherein the derivative is a soybean plant derived from crosses involving line W20 as a parent.

11. A method according to Preferred 7 wherein the derivative is a soybean plant derived from crosses involving line W4—4 as a parent.

12. A method according to Preferred 5 wherein the cotton plant is selected from the group consisting of lines 19-51A, 19-58b, 19-58c, 19-94, 19-114a, 19-114b, 20-10, 25-2, 25-5, 20-32, 25-1, B6D4a and derivatives thereof.

13. A method according to Preferred 12 wherein the cotton is 19-51a.

14. A method according to Preferred 12 wherein the cotton is B6D-4a.

15. A method according to Preferred 12 wherein the cotton is 20-10.

16. A method according to Preferred 12 wherein the cotton is 25-2.

17. A method according to Preferred 12 wherein the cotton is 25-5.

18. A method according to Preferred 12 wherein the cotton is derived from 19-51a.

19. A method according to Preferred 12 wherein the cotton is derived from B6D-4a.

20. A method according to Preferred 12 wherein the cotton is derived from 20-10.

21. A method according to Preferred 12 wherein the cotton is derived from 25-2.

22. A method according to Preferred 12 wherein the cotton is derived from 25-5.

DETAILED DESCRIPTION OF THE INVENTION

Synthesis

The compounds of the present invention may be prepared as indicated in the following specific synthetic examples by one skilled in the art.

The pyrimidine carbamates used in this invention are prepared as disclosed in EP-A-44,807, EP-A-72347, EP-A-173498, U.S. Pat. No. 4,666,506 and references cited therein.

Methyl 2-[[[[[4,6-bis(difluoromethoxy)-2-pyrimidinyl]amino]-carbonyl]amino]sulfonyl]benzoate (compound 3) is prepared as taught in U.S. Pat. No. 4,478,635 and references cited therein.

Agriculturally suitable salts of compounds of the present invention (compounds 1–3) are also useful herbicides and can be prepared in a number of ways known in the art. For example, metal salts can be made by contacting compounds of the present invention (compounds 1-3) with a solution of an alkali or alkaline earth metal salt having a sufficiently basic anion (e.g., hydroxide, alkoxide, carbonate or hydride). Quaternary amine salts can be made by similar techniques.

Salts of compounds of the present invention (compounds 1-3) can also be prepared by exchange of one cation for another. Cationic exchange can be effected by direct contact of an aqueous solution of a salt of a compound of the present invention (compounds 1-3) (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of the present invention (compounds 1-3) (e.g., an alkali metal or quaternary amine salt) through a column packed with a cation exchange resin containing the cation to be exchanged for that of the original salt and the desired product is eluted from the column. This method is particularly useful when the desired salt is watersoluble (e.g., a potassium, sodium or calcium salt).

Acid addition salts, useful in this invention, can be obtained by reacting a compound of the present invention (compounds 1-3) with a suitable acid, e.g., p-toluenesulfonic acid, trichloroacetic acid or the like.

Temperatures are reported in degrees Celsius. Abbreviations for nuclear magnetic resonance (NMR) are: s-singlet, d-doublet, t-triplet, m-multiplet, brs-broad singlet. NMR peak positions are reported as parts per million downfield from internal tetramethylsilane. Infrared (IR) peak positions are given in reciprocal centimeters ($cm^{-1}$).

TABLE I

| Compound | $R^1$ | $R^2$ | $R^3$ | $R^4$ | E |
|---|---|---|---|---|---|
| 1 | Cl | $CHFCH_3$ | $CH_3$ | $OCH_3$ | N |
| 2 | Cl | $C(O)OCH(CH_3)_2$ | $CH_3$ | $CH_3$ | CH |
| 3 | H | $C(O)OCH_3$ | $OCF_2H$ | $OCF_2H$ | CH |

SYNTHESIS OF COMPOUND 1

2-Chloro-6-(1-Fluoroethyl)-N-[[(4-Methoxy-6-Methyl1,3,5-Triazin-2-Yl)Amino]Carbonyl]Benzenesulfonamide (A) 3-Chloro-2-Phenylmethylthiobenzaldehyde To a suspension of potassium t-butoxide (32 g) in 170 mL of dimethylformamide (DMF) at room temperature was added benzyl mercaptan (34 mL) while maintaining the temperature at 20°. The reaction mixture was stirred an additional 1 h and then 2,3-dichlorobenzaldehyde (50 g) was added portionwise. The reaction was allowed to stir overnight at room temperature and then poured into excess water/ice. The solids were collected and air dried to provide 40 g of the title compound, mp 68°-70°.

90 MHz NMR ($CDCl_3$)δ: 4.00 (s, 2H, $CH_2$); 6.80-7.40 (m, 6H, arom); 7.70 (d, 2H, arom); and 10.25 (s, 1H, aldehyde).

(B) 3-Chloro-α-Methyl-2-Phenylmethylthiobenzenemethanol

To a solution of 3-chloro-2-phenylmethylthiobenzaldehyde (53 g) in 670 mL of tetrahydrofuran (THF) at 0° was added 78.7 mL of a 2.7 M solution of methylmagnesium bromide dropwise. The reaction was allowed to come to room temperature and stirred overnight. The reaction mixture was diluted with water and extracted with ethyl acetate. The organic phase was dried over magnesium sulfate filtered, and concentrated to provide 55 g of an oil which was suitable for use in the next reaction.

90 MHz NMR ($CDCl_3$)δ: 1.20 (d, 3H, $CH_3$); 1.50 (brs, 1H, OH); 4.00 (s, 2H, benzyl); 1.12 (q,1H); and 6.85–7.55 (m, 8H, arom).

(C) 3-Chloro-2-Phenylmethylthio-(1-Fluoroethyl)Benzene

To a solution of diethylaminosulfur trifluoride (10.3 mL) in 80 mL of methylene chloride at −78° was added a solution of 3-chloro-α-methyl-2-phenyl methylthiobenzenemethanol (23 g) in a minimum amount of methylene chloride dropwise. The reaction was allowed to slowly warm to room temperature and then poured onto ice. The aqueous phase was extracted with excess methylene chloride and the combined organic phase was dried over magnesium sulfate, filtered and concentrated to provide an orange oil. Column chromatography on silica gel (elution with 2% ethyl acetate/hexanes) yielded 16.41 g of the title compound as a light yellow oil.

90 MHz NMR ($CDCl_3$) δ: 1.50 (dd, 3H, $CH_3$); 4.15 (s, 2H, benzyl); 6.05 (dd, 1H, benzylic-H); and 7.13–7.75 (m, 8H, arom).

(D) 2-Chloro-6-(1-Fluoroethyl)Benzenesulfonamide

To a solution of 8.0 g of 3-chloro-2-phenylmethylthio-(1-fluoroethyl)benzene in a mixture of 45 mL of propionic acid and 1.5 mL of water at −10° was added 5.2 mL of liquified chlorine. The reaction was stirred an additional 30 min and then poured into a mixture of ice/water. The aqueous phase was extracted with n-butyl chloride and the combined organic phase was washed with saturated sodium bicarbonate solution, dried over magnesium sulfate and concentrated to provide an oil. The crude sulfonyl chloride was dissolved in 100 mL of THF, cooled to −78° and treated with 1.6 mL of liquified anhydrous ammonia. The reaction was allowed to slowly warm to room temperature and stirred overnight. The solids were removed by filtration and then concentration provided the crude sulfonamide. Recrystallization from ethanol/water yielded 2.7 g of the title compound as a white solid, mp 151°–153°.

200 MHz NMR ($CDCl_3$) δ: 1.55 (dd, 3H, $CH_3$); 6.40–6.55 (m, 2.5H, $NH_2$ and CHF); 6.76 (q, 0.5H, CHF); 7.40 (d, 2H, arom); and 7.58 (t, 1H, arom).

(E) 2-Chloro-6-(1-Fluoroethyl)-N-[[(4-Methoxy-6-Methyl-1,3,5-Triazin-2-YL)Amino]Carbonyl] Benzenesulfonamide To a solution of 0.24 g of 2-chloro-6-(1-fluoroethyl)-benzenesulfonamide and 0.26 g of O-phenyl-N-(4-methoxy-6-methyl-1,3,5-triazin-2-yl) carbamate in 5.0 mL of acetonitrile at room temperature was added 1,8-diazabicyclo[5.4.0]undec-7-ene (0.15 mL). The reaction was stirred an additional 1 h at room temperature, then diluted with water (5.0 mL) and acidified to pH 4 with 1N hydrochloric acid. The resulting precipitate was collected by filtration, washed with water and air dried to give 0.23 g of the title compound as a white solid, mp 181°–183°.

200 MHz NMR (CDCl3) δ: 1.68 (dd, 3H, CH3); 2.45 (s, 3H, CH3); 3.96 (s, 3H, OCH3); 6.76 (dd, 1H, CHF); and 7.6–7.82 (m, 3H, arom).

SYNTHESIS OF COMPOUND 2

1-Methylethyl 3-Chloro-2-[[[[(4,6-Dimethyl-2-Pyrimidinyl)Amino]-Carbonyl]Amino]Sulfonyl]Benzoate

(1) 2Propyl-3-Chloro-2-Nitrobenzoate

A solution of 10.582 g (52.5 mmol) of commercial 3-chloro-2-nitrobenzoic acid in 300 mL of 2-propanol was charged with 45 mL of conc. $H_2SO_4$, and the resulting mixture was heated to reflux for 3.75 days. The reaction vessel was fitted with a distillation head and approximately 150 mL of 2-propanol was distilled from the reaction mixture. The remaining reaction mixture was poured slowly in 300 mL of sat. $NaHCO_3$(aq). Methylene chloride (100 mL) was added along with approximately 5 g of NaOH (to keep the aqueous layer basic), and some ice to reduce the temperature.

The layers were separated, and the aqueous layer was extracted with 3×80 mL of methylene chloride. The combined organic portions were extracted with 150 mL of water and 150 mL of brine, and were dried ($MgSO_4$) and concentrated to give 9.28 g (73%) of the title compound as a light orange liquid.

NMR δ: 1.33 (d, 6H J=7.5 Hz); 5.19 (heptet, 1H, J=7.5 Hz); 7.5–7.77 (m, 2H); and 7.95 (dd, 1H, J=2.0, 7.5 Hz).

(2) 2-Propyl 2-Phenylmethylthio-3-Chlorobenzoate

A 500 mL 3-neck round-bottom flask equipped with a thermometer, nitrogen inlet septum and magnetic stirbar was charged with 1.505 g of a 35% suspension of potassium hydride in mineral oil (13.1 mmol, 1.6 eq), and this was taken up in 30 mL of anhydrous THF. The resulting mixture was cooled to −20°, and was then charged by syringe with 1.25 mL of benzylmercaptan (10.7 mmol, 1.3 eq). The resulting mixture was allowed to come to 10°, stirred for 1 h, and then cooled to −12°. The resulting white slurry was charged via dropping funnel with a solution of 2.000 g of 2-propyl 3-chloro-2-nitrobenzoate (8.21 mmol) in a total of 9.5 mL of THF, to give a brown slurry. This was allowed to come to room temperature and was stirred for 20 h.

The reaction mixture was poured into 100 mL of a 1:1 mixture of 6N NaOH(aq) and brine, and extracted three times with ethyl acetate. The combined organics were extracted with brine, dried ($MgSO_4$) and concentrated to give 5.04 g of a clear light brown liquid.

The crude product was chromatographed on silica (20% acetone/hexanes) to give two fractions:

Fraction 1: 122 mg of an orange solid, shown by 1H-NMR to lack the 2-propyl ester—not further investigated.

Fraction 2: 2.07 g (79%) of the title compound as an orange oil:

NMR δ: 1.38 (d, 6H J=7.5 Hz); 4.10 (s, 2H); 5.20 (m, 1H); 7.25 (s, 5H); and 7.1–7.7 (m, 3H).

(3) 3-Chloro-1-(2-Propyloxycarbonyl)Phenyl-2-Sulfonyl Chloride

A 1-L 4-neck round-bottom flask equipped with a mechanical stirrer, dropping funnel, thermometer and stopper was charged with 8.857 g of 2-propyl 2-phenylmethylthio-3-chlorobenzoate (27.6 mmol) in a total of 200 mL of methylene chloride, 55 mL of water and 8 mL of conc. HCl, and the resulting mixture was cooled to approximately 0° in an ice/water/NaCl bath. To this mixture was added slowly 130 mL of commercial Clorox® bleach (91 mmol, 3.3 eq) over 45 min keeping the temperature between 0°–5°. Stirring was continued at 0° for an additional 1.5 h after the addition was finished.

The layers were separated, and the aqueous layer extracted with 2×50 mL of methylene chloride, and the combined organics were extracted with 150 mL of brine, dried ($MgSO_4$) and concentrated to give 11.81 g of a golden-colored liquid.

The crude product was chromatographed on 300 g of silica (10% acetone/petroleum ether, increasing to 15%, 20%, 33%) to give 7.824 g (95%) of the title compound as a clear yellow liquid:

NMR δ: 1.39 (d, 6H J=7.5 Hz); 5.28 (heptet, 1H, J=7.5 Hz); 7.4–7.65 (m, 1H); and 7.65–7.82 (m, 2H).

(4) 3-Chloro-1-(2-Propyloxycarbonyl)Phenyl-2-Sulfonamide

A solution of 2.100 g of 3-chloro-1-(2-propyloxycarbonyl)phenyl-2-sulfonyl chloride (7.07 mmol) in 60 mL of acetonitrile was chilled in a cold water bath and charged over the surface of the solution with a gentle stream of gaseous $NH_3$ through a glass pipette. The progress of the reaction was monitored by thin-layer chromatography (TLC), and, when judged complete, the resulting suspension was vacuum filtered, and the filter cake was rinsed with additional acetonitrile. Concentration of the acetonitrile solution yielded 1.912 g (97%) of the title compound as a light beige solid, mp 155°–158°:

NMR δ: 1.33 (d, 6H J=7.5 Hz); 5.19 (heptet, 1H, J=7.5 Hz); 6.90 (brs, 2H); 7.35–7.55 (m, 1H); and 7.65–7.8 (m, 2H).

(5) 1-Methylethyl 3-Chloro-2-[[[[(4,6-Dimethyl-2-Pyrimidinyl)Amino]-Carbonyl]Amino]Sulfonyl] Benzoate A solution of 602 mg of 3-chloro-1-(2-propyloxycarbonyl)phenyl-2-sulfonamide (2.17 mmol) and 539 mg of the N-(phenoxycarbonyl)-2-amino-4,6-dimethylpyrimidine (2.22 mmol, 1.02 eq) in 30 mL of dry acetonitrile was chilled in a cold water bath and charged by syringe with 340 μL of 1,8-diazobicyclo[5.4.0]dec-7-ene (2.27 mmol, 2.27 eq), and the resulting solution was stirred at room temperature for 3 h, at which time TLC indicated the absence of starting materials.

The reaction mixture was added dropwise to a well-stirred mixture of 250 mL of water and some ice. When the addition was complete, the quench mixture was cooled in an ice/water bath and treated with 1N HCl(aq) to pH 2–3, which gave a precipitate. This suspension was vacuum filtered and the resulting solids were dried in vacuo to give 898 mg of the crude sulfonylurea as a white solid.

A 450 mg portion of this product was chromatographed on 30 g of silica with 20% acetone/petroleum ether, increasing to 30% and 40%, to yield 209 mg of the title compound as a very viscous clear oil.

NMR δ: 1.34 (d, 6H J=7.5 Hz); 1.83 (brs, 1H); 2.46 (s, 6H); 5.20 (heptet, 1H, J=7.5 Hz); 6.96 (s, 1H); 7.4-7.7 (m, 3H); and 9.48 (brs, 1H).

This was taken up in 2 mL of acetonitrile and added dropwise to 20 mL of chilled 0.1N Hcl(aq). The resulting suspension was filtered and the solids dried in vacuo to yield 173 mg of the title compound, mp 158°-160°.

The remaining 285 mg of crude sulfonylurea was chromatographed and reprecipitated as described above to yield 252 mg of the title compound as a white solid, mp 155°-156°. [total yield: 425 mg (46%)].

Formulations

Useful formulations of the compounds this invention can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

|  | Weight Percent* | | |
| --- | --- | --- | --- |
|  | Active Ingredient | Diluent(s) | Surfacants(s) |
| Wettable Powders | 20-90 | 0-74 | 1-10 |
| Oil Suspensions, Emulsions, Solutions (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a surfactant or a diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, N.Y., 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1963, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, June 23, 1959, Col. 3, line 66 through Col. 5, line 17 Examples 1-4;

G. C. Klingman, "Weed Control as a Science", John Wiley and Sons, Inc., New York, 1961, pp. 81-96; and J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE A

| High Strength Concentrate | |
| --- | --- |
| 2-chloro-6-(1-fluoroethyl)-N-[[(4-methoxy-6-methyl-1,3,5-triazin-2-yl)amino]carbonyl]-benzenesulfonamide | 99% |
| trimethylnonyl polyethylene glycol ether | 1% |

The surfactant is sprayed upon the active ingredient in a blender and the mixture sifted through a U.S.S. No. 40 sieve (0.42 mm openings) prior to packaging. The concentrate may be formulated further for practical use.

EXAMPLE B

| Wettable Powder | |
| --- | --- |
| 2-chloro-6-(1-fluoroethyl)-N-[[(4-methoxy-6-methyl-1,3,5-triazin-20yl)amino]carbonyl]-benzenesulfonamide | 65% |
| dodecylphenol polyethylene glycol ether | 2% |
| sodium ligninsulfonate | 4% |
| sodium silicoaluminate | 6% |
| montmorillonite (calcined) | 23% |

The ingredients are thoroughly blended. The liquid surfactant is added by spraying upon the solid ingredients in the blender. After grinding in a hammer mill to produce particles essentially all below 100 microns, the material is reblended and sifted through a U.S.S. No. 50 sieve (0.3 mm opening) and packaged.

EXAMPLE C

| Aqueous Suspension | |
|---|---|
| 2-chloro-6-(l-fluoroethyl)-N-[[(4-methoxy-6-methyl-1,3,5-triazin-2-yl)amino]carbonyl]-benzenesulfonamide | 50.0% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE D

| Oil Suspension | |
|---|---|
| 2-chloro-6-(l-fluoroethyl)-N-[[(4-methoxy-6-methyl-1,3,5-triazin-2-yl)amino]carbonyl]-benzenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 3 microns. The product can be used directly, extended with oils, or emulsified in water.

EXAMPLE E

| Oil Suspension | |
|---|---|
| 2-chloro-6-(l-fluoroethyl)-N-[[(4-methoxy-6-methyl-1,3,5-triazin-2-yl)amino]carbonyl]-benzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE F

| Aqueous Suspension | |
|---|---|
| 2-chloro-6-(l-fluoroethyl)-N-[[(4-methoxy-6-methyl-1,3,5-triazin-2-yl)amino]carbonyl]-benzenesulfonamide | 25% |
| hydrated attapulgite | 3% |
| crude calcium ligninsulfonate | 10% |
| sodium dihydrogen phosphate | 0.5% |
| water | 61.5% |

The ingredients are ground together in a ball or roller mill until the solid particles have been reduced to diameters under 10 microns.

EXAMPLE G

| Aqueous Suspension | |
|---|---|
| 2-chloro-6-(l-fluoroethyl)-N-[[(4-methoxy-6-methyl-1,3,5-triazin-2-yl)amino]carbonyl]-benzenesulfonamide | 40.0% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm opening) before packaging.

All compounds of the invention may be formulated in the same manner.

EXAMPLE H

| Granule | |
|---|---|
| wettable powder of Example G | 15% |
| gypsum | 69% |
| potassium sulfate | 16% |

The ingredients are blended in a rotating mixer and water sprayed on to accomplish granulation. When most of the material has reached the desired range of 1.0 to 0.42 cm (U.S.S. #18 to 40 sieves), the granules are removed, dried, and screened. Oversized material is crushed to produce additional material in the desired range. These granules contain % active ingredient.

EXAMPLE I

| Wettable Powder | |
|---|---|
| 2-chloro-6-(l-fluoroethyl)-N-[[(4-methoxy-6-methyl-1,3,5-triazin-2-yl)amino]carbonyl]-benzenesulfonamide | 50.0% |
| sodium alkylnaphthalenesulfonate | 2% |
| low viscosity methyl cellulose | 2% |
| diatomaceous earth | 46% |

The ingredients are blended, coarsely hammer-milled and the air milled to produce particles of active essentially all below 10 microns in diameter. The product is reblended before packaging.

EXAMPLE J

| Extruded Pellet | |
|---|---|
| 2-chloro-6-(l-fluoroethyl)-N-[[(4-methoxy-6-methyl-1,3,5-triazin-2-yl)amino]carbonyl]-benzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE K

| Wettable Powder | |
|---|---|
| 2-chloro-6-(1-fluoroethyl)-N-[[(4-methoxy-6-methyl-1,3,5-triazin-2-yl)amino]carbonyl]-benzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended and then ground in a hammermill to produce particles with an average particle size less than 25 microns in diameter. The material is reblended and sifted through a U.S.S. No. 50 sieve (0.3 mm opening) before being packaged.

EXAMPLE L

| High Strength Concentrate | |
|---|---|
| 2-chloro-6-(1-fluoroethyl)-N-[[(4-methoxy-6-methyl-1,3,5-triazin-2-yl)amino]carbonyl]-benzenesulfonamide | 98.5% |
| silica aerogel | 0.5% |
| synthetic amorphous fine silica | 1.0% |

The ingredients are blended and ground in a hammer mill to produce a high strength concentrate essentially all passing a U.S.S. No. 50 sieve (0.3 mm openings). This material may then be formulated in a variety of ways.

EXAMPLE M

| Solution | |
|---|---|
| 2-chloro-6-(1-fluoroethyl)-N-[[(4-methoxy-6-methyl-1,3,5-triazin-2-yl)amino]carbonyl]-benzenesulfonamide, sodium salt | 5% |
| water | 95% |

The salt is added directly to the water with stirring to produce the solution, which may then be packaged for use.

UTILITY

Compounds of this invention are highly active herbicides useful for the preemergence and/or postemergence control of broadleaf and grass weeds that commonly infest soybean and cotton fields. The compounds of this invention are valued due to their low use rates required, their broad spectrum of activity (especially on key broadleaf weeds), and/or their favorable soil dissipation rates. The compounds are particularly valued for their selective tolerance by soybean and cotton plants containing at least one gene that confers resistance to inhibitors of acetolactate synthase. The compounds would similarly be useful on other crops that are "gene-altered" for the purpose of providing crop tolerance; for example, the crops disclosed in EP-A-154,204, particularly corn (*Zea mays L.*)

TEST DESCRIPTION

Seeds of lines W20 and W4—4 of gene-modified soybeans (*Glycine max*), lines B6D-4a, 19-51a and 20-10 of gene-modified cotton (*Gossypium hirsutum*), Pioneer 3377 Ex corn (*Zea mays L.*), cocklebur (*Xanthium pensylvanicum*), morningglory (*Ipomoea hederacea*), velvetleaf (*Abutilon theophrasti*), barnyardgrass (*Echinochloa crus-galli*), johnsongrass (*Sorghum halepense*), and foxtail (*Setaria faberii*) were planted in a sandy loam and treated preemergence with test chemicals (Compounds of Table 1) dissolved in a non-phytotoxic solvent. After spraying, the soil surface was sprinkled with water to simulate rainfall. Treated plants and controls were maintained in a greenhouse for approximately four weeks, then all species were compared to untreated controls and visually evaluated. The species above were also planted in potting mixture and grown in the greenhouse for 2 weeks to the 1-3 leaf stage, then sprayed postemergence. After spraying, the plants were held in the greenhouse approximately 3 weeks before being visually evaluated. The plant response ratings, summarized in Tables A and B are based on a scale of 0 to 10, where 0 is no effect and 10 is complete control. A dash (-) response means no test result. Responses of 5 individual plants of cotton line 20-10 were recorded in Table B as (1), (2), (3), (4), and (5) since the line was an R1 population segregating for herbicide resistance. Plant responses on line 20-10 at each rate of treatment were arranged from lowest to highest with the assumption that plants showing no effect carried gene(s) conferring resistance while those injured carried fewer or no genes conferring resistance.

TABLE A

| CMPD | RATE G/HA | SOYBEAN W20 | COCKLE-BUR | MORNING GLORY | VELVET LEAF | BARN-YARD-GRASS | JOHNSON GRASS | GIANT FOXTAIL |
|---|---|---|---|---|---|---|---|---|
| PREEMERGENCE | | | | | | | | |
| 1 | 4 | — | 7 | 9 | 8 | 10 | 10 | 5 |
| 1 | 16 | 0 | 9 | 10 | 10 | 10 | 10 | 9 |
| 1 | 32 | — | 10 | 10 | 10 | 10 | 10 | 10 |
| 1 | 64 | 3 | — | — | — | — | — | — |
| 1 | 125 | 5 | — | — | — | — | — | — |
| 2 | 4 | — | 8 | 2 | 0 | 9 | 10 | 6 |
| 2 | 16 | 0 | 9 | 9 | 8 | 10 | 10 | 6 |
| 2 | 32 | — | 9 | 10 | 9 | 10 | 10 | 10 |
| 2 | 64 | 0 | — | — | — | — | — | — |
| 2 | 125 | 3 | — | — | — | — | — | — |
| 3 | 31 | 0 | 9 | 8 | 9 | — | 10 | 6 |
| 3 | 62 | 0 | 9 | 9 | 10 | — | 10 | 10 |
| 3 | 125 | 0 | 10 | 9 | 10 | — | 10 | 10 |
| 3 | 250 | 0 | 10 | 10 | 10 | — | 10 | 10 |
| POSTEMERGENCE | | | | | | | | |
| 1 | 1 | 0 | 7 | 6 | 6 | 6 | 6 | — |
| 1 | 2 | 2 | 10 | 10 | 8 | 7 | 9 | — |
| 1 | 4 | 4 | 10 | 10 | 10 | 10 | 10 | — |
| 1 | 8 | 5 | 10 | 7 | 6 | — | 10 | 5 |

TABLE A-continued

| CMPD | RATE G/HA | SOYBEAN W20 | COCKLE-BUR | MORNING GLORY | VELVET LEAF | BARN-YARD-GRASS | JOHNSON GRASS | GIANT FOXTAIL |
|---|---|---|---|---|---|---|---|---|
| 1 | 16 | 7 | 10 | 10 | 10 | — | 10 | 8 |
| 1 | 31 | 9 | 10 | 10 | 10 | — | 10 | 10 |
| 2 | 1 | 0 | 9 | 5 | 3 | 0 | 5 | — |
| 2 | 2 | 0 | 10 | 6 | 7 | 5 | 7 | — |
| 2 | 4 | 0 | 10 | 7 | 10 | 6 | 10 | — |
| 2 | 8 | 2 | 10 | 10 | 10 | 7 | 10 | — |
| 3 | 16 | 1 | 10 | 5 | 6 | — | 10 | 5 |
| 3 | 31 | 2 | 10 | 5 | 9 | — | 10 | 6 |
| 3 | 62 | 7 | 10 | 8 | 10 | — | 10 | 7 |
| 3 | 125 | 7 | 10 | 9 | 10 | — | 10 | 10 |

TABLE B

| CMPD | RATE G/HA | SOYBEAN W4-4 | COTTON B6D-4a | COTTON 19-51a | CORN PIONEER 3377EX | COTTON 20-10 (1) | (2) | (3) | (4) | (5) |
|---|---|---|---|---|---|---|---|---|---|---|
| PREEMERGENCE ||||||||||||
| 1 | 8 | 0 | 0 | 0 | 0 | 0 | 0 | 0 | 0 | 4 |
| 1 | 16 | 0 | 0 | 0 | 1 | 0 | 0 | 0 | 0 | 0 |
| 1 | 31 | 0 | 0 | 0 | 3 | 0 | 0 | 0 | 0 | 0 |
| 1 | 62 | 1 | 0 | 0 | 4 | 0 | 0 | 0 | 0 | 3 |
| 3 | 31 | 0 | 0 | 0 | 0 | 0 | 0 | 0 | 0 | 0 |
| 3 | 62 | 0 | 0 | 0 | 0 | 0 | 0 | 0 | 3 | 9 |
| 3 | 125 | 0 | 0 | 0 | 0 | 0 | 0 | 0 | 0 | 0 |
| 3 | 250 | 0 | 0 | 0 | 0 | 0 | 0 | 0 | 3 | 0 |
| POSTEMERGENCE ||||||||||||
| 1 | 1 | 0 | — | 0 | 2 | — | — | — | — | — |
| 1 | 2 | 0 | — | 0 | 4 | — | — | — | — | — |
| 1 | 4 | 1 | — | 1 | 8 | — | — | — | — | — |
| 1 | 8 | 2 | 0 | — | 9 | 0 | 0 | 0 | 0 | 0 |
| 1 | 16 | 3 | 3 | — | 10 | 0 | 0 | 0 | 0 | 1 |
| 1 | 31 | 5 | 4 | — | 10 | 0 | 0 | 2 | 3 | 4 |
| 2 | 1 | 0 | — | 0 | 0 | — | — | — | — | — |
| 2 | 2 | 0 | — | 0 | 0 | — | — | — | — | — |
| 2 | 4 | 0 | — | 0 | 1 | — | — | — | — | — |
| 2 | 8 | 1 | — | 1 | 2 | — | — | — | — | — |
| 3 | 16 | 0 | 0 | — | 0 | 0 | 0 | 0 | 0 | 10 |
| 3 | 31 | 0 | 2 | — | 0 | 0 | 0 | 0 | 0 | 0 |
| 3 | 62 | 0 | 4 | — | 0 | 0 | 0 | 0 | 0 | 0 |
| 3 | 125 | 1 | 7 | — | 0 | 0 | 0 | 0 | 0 | 3 |

Herbicide-Resistant Plants

Soybean

Plants particularly useful in the method of the instant invention include soybean and cotton plants that contain at least one gene that confers resistance to inhibitors of acetolactate synthase. Included among such plants are soybean lines W20 and W4—4 which have been deposited under the terms of the Budapest Treaty with the American Type Culture Collection, Rockville, MD and bear the accession numbers 40467 and 40650, respectively. Additionally, the production of soybean line W20 has been described by Sebastian et al. [(1989) Crop Sci. 29:1403-1408]. Both of these lines contain the Als1 gene.

The Als1 allele can be transferred from soybean line W20 to other lines using conventional breeding practices. Since Als1 is a single semidominant allel [Sebastian et al. (1989) Crop Sci. 29:1403-1408], segregation of resistance is very predictable. For example, when W20 is crossed with a soybean line sensitive to sulfonylurea herbicides, F2 progeny will segregate to yield approximately ¼ homozygous resistant: ½ heterozygous intermediate: ¼ homozygous sensitive. Differentiating between these three types of segregants can be done using the hydroponic procedure described by Sebastian et al. [(1986) Crop Sci. 29:1403-1408] or by using one of the following procedures:

Seed Soak Screen

This method is ideal for greenhouse screening but can also be used for field plantings. Seeds (for example, an F2 population) are placed on germination paper wetted with an aqueous solution of 1 mg/L chlorsulfuron (2-chloro-N-[(4-methoxy-6-methyl-1,3,5-triazin-2-yl)aminocarbonyl]benzenesulfonamide). Seeds are allowed to imbibe the herbicide solution overnight (at least 12 to 16 h). Seeds are then removed from the germination paper and rinsed briefly with water to remove exogenous herbicide. Any seeds that are not fully imbibed must be discarded as hard seeds will be "escapes" since they did not take up any herbicide. Imbibed seeds are then planted in the greenhouse or in the field and irrigated to prevent desiccation. Within one week, viable seeds will emerge. However, sensitive seedlings will not develop any further than expansion of the cotyledons. Homozygous-resistant seedlings will grow normally. Heterozygotes will have wrinkled unifoliolate leaves but will eventually recover and grow normally. At 14 to 21 days after planting, any unwanted segregants (including heterozygotes, if desired) can be rogued out. For seed purification purposes, it is advisable to rogue out all unwanted plants; occasionally, some of the sensitive plants will make a weak recovery and produce a few seeds. If possible, use homozygous resistant plants to continue the next cycle of backcrossing. Progeny testing is advisable if putative homozygotes are to be combined to form a true-breeding line.

Small Scale Postemergence Screen

This method is ideal for screening plants that have already emerged. It can be used in the greenhouse and in small field plots. Recommended herbicide rates are given. However, injury of a given genotype may vary somewhat depending on how consistently the plants are sprayed.

Seedlings are grown until the first trifoliolates are fully open. A 5 mg/L solution of chlorsulfuron containing 0.2 mL/LX-77 ® (or similar wetting agent) is prepared and sprayed to run-off using a hand-held sprayer. Within 10 to 14 days, sensitive soybean plants should be severely injured and dying. Injury will appear as death of terminal buds and reddening of the leaf veins followed by necrosis of the leaves. Homozygous resistant plants will be unaffected or only slightly stunted. Heterozygous plants should be distinguishable by their intermediate response. At 14 days after treatment, dead or dying plants can be rogued out. Selection for the best looking plants will generally identify the homozygous resistant individuals. However, progeny testing should be performed for confirmation.

For screening backcross progenies where only heterozygous resistant and homozygous sensitive plants are present, a lower rate of chlorsulfuron (for example, 2 mg/L) should be used in the postemergence screen. Lower rates of chlorsulfuron should still kill sensitive plants while leaving the heterozygotes in better condition for crossing or propagation.

Postemergence Field Screen

This method is ideal for screening large populations under field conditions. This screen is efficient but may result in some "escapes" depending on the plant density and on the extent of spray coverage. This screen is not recommended unless a few "escapes" can be tolerated.

Soybeans are planted at no more than 6 to 8 seeds per foot; closer spacing increases the likelihood of "escapes" due to shading. At the second trifoliolate stage, the field is sprayed with 8 g/ha chlorsulfuron. A wetting agent such as X-77 ® is added at 2.5 mL/L of spray solution. The spray volume is 187 L/ha. For good coverage Spraying Systems, Inc. 8002 flat fan nozzles at 40 psi spaced according to the manufacturer's recommendation (approximately 19-20 inches apart) for good herbicide coverage are used. At 14 to 21 days after treatment, sensitive plants will be severely injured or dead. Heterozygous plants may be somewhat injured but will recover. All undesirable segregants should be rogued out to ensure that they will not recover. The plants that are the least injured are most probably the resistant homozygotes.

The Als1 gene can be transferred from line W4—4 to other soybean lines. When an F2 population from the cross W4—4 X A3205 (a sensitive variety) was screened hydroponically [as described by Sebastian et al. (1989) Crop Sci. 29:1403-1408] with 100 mg/L chlorsulfuron, 10 out of 164 F2 plants (approximately 1/16 of the F2) were completely sensitive to chlorsulfuron. This indicates that W4—4 has two genes for sulfonylurea tolerance. This test (along with additional tests) indicates that W4—4 is homozygous for both Als1 plus another semidominant gene (Als2) that segregates independently of Als1. Als2 affects resistance of acetolactate synthase to sulfonylurea herbicides such as chlorsulfuron but resides at a second locus independent of Als1.

Knowing this digenic inheritance pattern makes breeding for resistance predictable to one skilled in the art. Transferring both resistance genes from W4—4 to other soybean lines can be done by hybridizing W4—4 with a sensitive soybean line and then screening segregating populations (for example, an F2) for resistance. F2 plants from a W4—4 X sensitive cross should segregate 1/16 homozygous sensitive:14/16 intermediate (a mixture of various heterozygotes):1/16 homozygous resistant. When screening this F2 population, it is necessary to choose an herbicide treatment that will identify plants that are homozygous for both Als1 and Als2. This can be done as follows:

A population of seed (for example, an F2 population) is placed in an immersible mesh bag. The bags are immersed and soaked for 16 h in an aqueous solution of 2 mg/L methyl 2-[[[[(4,6-dimethoxy-2-pyrimidinyl)amino-carbonyl]amino]sulfonyl]-3-pyridinecarboxylate (EP-A-314,302). The solution is kept under continuous aeration through the use of an "air stone" supplied with air from a standard aquarium pump. During the soaking period, the seeds imbibe both water and the dissolved herbicide. After the soaking period, the seeds are immersed in tap water for two minutes to remove exogenous herbicide solution. A planting bed is then created by filling a greenhouse pallet with a peat-based soil mixture. The soil mixture is leveled at 7 cm deep by dragging a flat board across the surface of the mixture. Prior to planting, the 7 cm soil mixture is thoroughly moistened by sprinkling the upper surface with tap water. Excess water is allowed to drain through. The herbicide-treated seeds are then planted out in a single horizontal layer at a density of approximately 12,000 seeds per square meter on the level planting bed. The seeds are then covered with a 2.5 cm level layer of coarse vermiculite. The described planting medium is kept moist by periodically sprinkling the upper surface of the planting medium with tap water. Viable seeds germinate, emerge and expand their cotyledons at approximately 8 days after planting. However, only plants homozygous for both Als1 and Als2 will develop normal leaves. Sensitive plants will form either no leaves at all or will form wrinkled, deformed leaves.

Cotton

Following are procedures useful in the production of transgenic cotton lines such as lines 19-51a, B6D-4a, 20-10, 25-2 and 25-5 on which the compounds and methods claimed herein are particularly useful. The origin of promoter chosen to drive the expression of the coding sequence is not critical as long as it has sufficient transcriptional activity to accomplish the expression of a sulfonylurea-resistant form of acetolactate synthase in cotton. Preferred promoters (besides the native tobacco acetolactate synthase promoter) for expression include those directing the 19S and 35S transcripts in Cauliflower Mosaic Virus [Odell et al. (1985) Nature 313:810-812; Hull et al. (1987) Virology 86:482-493], small subunit of ribulose 1,5-bisphosphate carboxylase [Morelli et al. (1985) Nature 315:200; Broglie et al. (1984) Science 224:838; Hererra-Estrella et al. (1984) Nature 310:115; Coruzzi et al. (1984) EMBO J. 3:1671; Faciotti et al. (1985) Bio/Technology 3:241] and chlorophyll a/b binding protein [Lampa et al. (1986) Nature 316:750-752]. Genes encoding mutant forms of acetolactate synthase that are resistant to sulfonylurea herbicides and therefore useful in these transformations are described in EP-A-257,993. Specifically described are the SURB-S4, SURA-C3 and SURB-Hra genes. Further, Lee et al. (EMBO J. 1988 7:1241-1248) describe the cloning of the SURB-Hra and SURA-C3 acetolactate synthase genes from tobacco (*Nicotiana tabacum*), the identification of the nucleotide changes responsible for sulfonylurea tolerance and the construction of Agrobacterium strains carrying those genes. The SURB-Hra gene, with its native tobacco promoter was used in the production of cotton line B6D-4a which is useful with the compounds and methods of the instant invention. Hartnett et al. (ACS Symposium Series Nos. 421, M. B. Green, W. K. Moberg and H. LeBaron, Eds. 1990. American Chemical Society, pp 459-473) describe the construction of chimeric tobacco genes coding for acetolactate synthase which is resistant to herbicides that inhibit the normal form of the enzyme.

The chimeric Hra ALS gene as taught by Hartnett et al. along with its native tobacco promoter was used in the production of cotton lines 19-51a, 19-58b, 19-58c, 19-94, 19-114a, 19-114b which are useful with the compounds and methods of the instant invention. Odell et al. (Plant Physiol. 1990 94:1647-1654) describe the use of the Cauliflower Mosaic Virus 35S promoter to regulate expression of acetolactate synthase genes in transgenic plants. The native tobacco promoter of the chimeric tobacco Hra ALS gene as taught by Hartnett et al. has been replaced with the Cauliflower Mosaic Virus 35S promoter and this construct was used in the production of cotton lines 20-10 and 20-32 which are useful with the compounds and methods of the instant invention.

The chimeric C3 gene was constructed by combining fragments of DNA from the SURA and SURB genes (EP-A-257,993). In addition, the native tobacco promoter was replaced with a portion of the Cauliflower Mosaic Virus 35S promoter to form the 35H gene. The SURA gene, with only 4 base pairs of 5' non-coding DNA included was subcloned into pUC119, and then a 0.42 kb Cauliflower Mosaic Virus 35S promoter fragment was ligated into a restriction site just upstream from the acetolactate synthase start codon. A mutation analogous to the C3 mutation (EP-A-257,993) was introduced into the SURB gene by site-directed mutagenesis. Finally, a restriction fragment from this modified gene was subcloned into the 35S-SURA gene. The mutation introduced into this gene results in a proline to glutamine substitution at amino acid position 191. The 35H chimeric gene was used in the production of cotton lines 25-1, 25-2 and 25-5 which are useful with the compounds and methods of the instant method.

Hypocotyl Transformation

A. Agrobacterium growth

Cultures of Agrobacterium are grown overnight in Minimal A Medium (see below) supplemented with the appropriate selectable antibiotic and started from a single colony (from a fresh streak). The morning of the transformation, the culture is diluted to $3 \times 10^8$ bacteria/mL. (Prior to dilution, bacteria should still be in log phase). The bacteria are allowed to grow to $6 \times 10^8$ bacteria/mL (early afternoon).

| Minimal A Medium (1 L) | |
|---|---|
| $K_2HPO_4$ | 10.5 g |
| KH$_2$PO$_4$ | 4.5 g |
| (NH$_4$)$_2$SO$_4$ | 1.0 g |
| Sodium citrate (dihydrate) | 0.5 g |
| Autoclave in 990 mL, then add sterile: | |
| MgSO$_4$OH$_2$O (1 M) | 1.0 mL |
| Glucose (20%) | 10.0 mL |

To solidify media: autoclave agar (15 g/L, Difco Bacto) in separate 500 mL volume. Then mix salts and agar before dispensing.

B. Explant Material

Cotton seedlings (7-10 day-old) grown in Magenta boxes (Magenta Corp., 4189 W. Montrose Ave., Chicago, IL 68641) are used as the explant material. Seeds are rinsed briefly in 70% ethanol, shaken in 30% Clorox ® for 30 min and rinsed three times with sterile distilled water. Water, containing 500 mg/L cefotaxime, is added to cover the seeds and the covered seeds are placed into a 30° C. incubator until the end of the day. The water/cefotaxime solution is changed once, and the seeds are left overnight in the incubator. Seed coats are removed and 2-4 seeds are placed in a Magenta box on Murashige and Skoog medium+500 mg/L cefotaxime solidified with 0.8% agar.

C. Transformation

The upper portions of the hypocotyl (of 7-10 day seedlings) are cut into 1 cm long sections, and split in half lengthwise. The Agrobacterium suspension is pipetted over the explants, and explants are placed onto cocultivation medium [T medium (see below)+100 uM acetosyringone] for 2-3 days at 24° C. The hypocotyls are then washed thoroughly in liquid T medium with 500 mg/l carbenicillin or cefotaxime. Typically, the explants are left on a shaker all day, changing the medium 4-6 times. The hypocotyls are then plated onto T medium+500 mg/L carbenicillin+50 mg/L chlorsulfuron.

Explants are transferred every 1-2 weeks for 6 weeks to fresh medium. Transformed calli should appear within 3 weeks. After 6 weeks, calli can be carefully removed (no explant material should be attached) and placed on T medium.

Calli are maintained on T medium, in low to moderate light, 16 h/8 h day/night cycle, 28° C. growth room. Cultures are transferred to fresh medium every 1-2 months. Embryogenesis may take 6 months or longer.

Any embryos that form can be put on EW medium. Embryos that are to mature into plants should be placed on EWZ medium after they are established on EW.

| T medium (1 L) | |
|---|---|
| Murashige and Skoog Salts (Sigma #M5524) | 4.31 g |
| 100X Gamborg B$_5$ vitamin stock (Sigma #G1019) | 1 mL |
| Glucose | 30 g |
| 2,4-D stock (1 mg/mL) | 100 μL |
| Kinetin stock (1 mg/mL) | 100 μL |
| MgCl$_2$.6H$_2$O | 0.75 g |
| pH to 5.8, add 1.6 g Gelrite (Merck & Co.), autoclave | |

| EW medium (1 L) | |
|---|---|
| Murashige and Skoog Salts | 4.31 g |
| Sucrose | 20 g |
| 100X Gamborg B$_5$ vitamins | 10 mL |
| KNO$_3$ | 1.9 g |

-continued

| | |
|---|---|
| MES buffer | 1.9 g |
| pH to 5.8, add 2 g Gelrite, autoclave | |

EWZ medium (1 L)

Same as EW above except 4 g of Gelrite is used instead of 2 g. Filter-sterilized chlorsulfuron stock is added only after the medium has been autoclaved and cooled to 55° C.

Maturation of Transformed Embryo Cultures

Embryos derived from hypocotyl transformation are maintained on EWZ medium, under moderate-to-high light conditions (1500-3000 lux), 16 h/8 h day/night cycle, 28° C. For maintaining transformed embryogenic cultures, 200 µg/L chlorsulfuron is added to the media after autoclaving.

Cultures are transferred every 2 weeks if chlorsulfuron has been added. The most mature embryos are selected unless they are obviously abnormal. Some small embryos should be transferred as well.

Conversion of Mature Embryos into Plants

Embryos on EWZ can be transferred into Magenta boxes containing SH medium when they are about 2 cm long. "Normal" embryos with cotyledons and a root system are most likely to convert into plants.

| SH medium (1 L)[1] | |
|---|---|
| 20 X SH macronutrients stock | 50 mL |
| 1000 X SH vitamins stock | 1 mL |
| 100 X SH micronutrients stock | 10 mL |
| Sucrose | 20 g |
| pH to 5.8, add 2 g Gelrite, autoclave, pour in sterile boxes | |

[1] See Stewart et al. Planta, 1977, 137:113-117.

Embryos are placed into Magenta boxes and cultured under high light (about 3000 lux) conditions, 16 h/8 h day/night cycle, in 28° C. growth room. Transfer is not necessary. Most embryos will not convert into plants, and may be discarded after 2-3 months if obviously abnormal.

Transferring Plants to the Greenhouse

Traits which indicate that a plant is ready for the greenhouse include an established root system, an established shoot system, leaves that are produced in a normal alternate pattern, and plants that are at least 2 inches tall. Plants are hardened, i.e. prepared for the greenhouse, using a moderately high humidity environment. Once the plants are in the greenhouse, they are monitored for abnormalities. Plants which are morphologically abnormal tend to be infertile. Plants with normal shedding of pollen have all proven to be fertile. All fertile plants are self-pollinated. Male sterile plants may be crossed with non-transformed plants. However, crossing success depends on the severity of the abnormalities of the male-sterile plant.

Testing Inheritance of Sulfonylurea Tolerance in Cotton

For each line to be tested, 20 delinted seeds are planted in a 10-inch bulb pan containing Metro-Mix 350 and watered thoroughly. Seeds which have not been delinted should be planted three days earlier. (Do not fertilize until the seedings emerge.) A wild-type control is included, both treated and untreated. Photoperiod should be 16 h/8 h light/day with temperature settings at 28° C. day and 24° C. night.

The pans are watered as necessary. Once the seedlings emerge they can be watered as needed with a nutrient solution such as Miracle-Gro (¼ teaspoon/8 L deionized water).

When seedlings have emerged and cotyledons have opened, 200 mL of a 100 µg/L chlorsulfuron/Miracle-Gro solution is applied to each pot except for the untreated wild-type control. The herbicide solution is poured along each row of seedlings, carefully wetting each one. Pans are maintained in trays with absorbant liners to prevent herbicide leakage. After two days, herbicide is applied as above. After another two days, herbicide is again applied as above.

Distinctions between the tolerant and sensitive seedlings should be apparent 7-10 days after the last treatment. Resistant seedlings develop normally, with formation and vigorous growth of true leaves. Sensitive seedlings display short hypocotyls, discolored cotyledons, and little or no true leaf formation. True leaves, if present, are small, yellow-green in color, and fail to unfurl completely.

Breeding methods useful in transferring altered acetolactate synthase genes from transgenic cotton lines to non-transgenic varieties are described in Poehlman, J. M. *Breeding Field Crops*, 3rd Ed., Avi Publishing Company, Inc., Westport, Conn., 1987.

Applicants believe that the disclosure presented above, along with the references cited herein are sufficient to teach one skilled in the art to produce the herbicide-resistant plants on which the compounds and methods of the instant invention are useful.

What is claimed is:

1. Compounds selected from the group consisting of 2-chloro-6-(1-fluoroethyl)-N-[[(4-methoxy-6-methyl-1,3,5-triazin-2-yl)amino]carbonyl]benzenesulfonamide,
1-methylethyl 3-chloro-2-[[[[(4,6-dimethyl-2-pyrimidinyl)amino]carbonyl]amino]sulfonyl]benzoate, and their agriculturally suitable salts.

2. The compound of claim 1 which is 2-chloro-6-(1-fluoroethyl)-N-[[(4-methoxy-6-methyl-1,3,5-triazin-2-yl)amino]carbonyl]benzenesulfonamide.

3. An agriculturally suitable composition for controlling the growth of undesired vegetation comprising an effective amount of a compound of claim 1 and at least one of the following: surfactant, solid or liquid diluent.

4. An agriculturally suitable composition for controlling the growth of undesired vegetation comprising an effective amount of a compound of claim 2 and at least one of the following: surfactant, solid or liquid diluent.

5. A method for controlling the growth of undesired vegetation which comprises applying to cotton or soybean plants containing at least one gene that confers resistance to inhibitors of acetolactate synthase an effective amount of a compound which is selected from the group consisting of
2-chloro-6-(1-fluoroethyl)-N-[[(4-methoxy-6-methyl-1,3,5-triazin-2-yl)amino]carbonyl]benzenesulfonamide,
1-methylethyl 3-cholro-2-[[[[(4,6-dimethyl-2-pyrimidinyl)amino]carbonyl]amino]sulfonyl]benzoate, and
methyl 2-[[[[[4,6-bis(difluoromethoxy)-2-pyrimidinyl]amino]carbonyl]amino]sulfonyl]benzoate.

6. The method of claim 5 wherein the compound is selected from the group consisting of 2-chloro-6-(1-fluoroethyl)-N-[[(4-methoxy-6-methyl-1,3,5-triazin-2-yl)amino]carbonyl]benzenesulfonamide and methyl 2-[[[[(4,6bis(difluoromethoxy)-2-pyrimidinyl]amino]carbonyl]amino]sulfonyl]benzoate.

7. The method of claim 5 wherein the compound is 2-chloro-6-(1-fluoroethyl)-N[[(4-methoxy-6-methyl-1,3,5-triazin-2-yl)amino]carbonyl]benzenesulfonamide.

8. The method of claim 5 wherein the compound is methyl 2-[[[[[4,6-bis(difluoromethoxy)-2-pyrimidinyl]amino]carbonyl]amino]sulfonyl]benzoate.

9. The method according to claims 5, 6, 7 or 8 in which the plant is soybean.

10. The method according to claims 5, 6, 7 or 8 in which the plant is cotton.

11. A method for controlling the growth of undesirable vegetation which comprises applying to a W20 or W4—4 soybean plant or derivatives thereof containing at least one gene selected from Als1 and Als2 that confers resistance to inhibitors of acetolactate synthase an effective amount of a compound which is selected from the group consisting of 2-chloro-6-(1-fluoroethyl)-N-[[(4-methoxy-6-methyl-1,3,5-triazin-2-yl)amino]carbonyl]benzenesulfonamide, 1-methylethyl 3-chloro-2-[[[[(4,6-dimethyl-2-pyrimidinyl)amino]carbonyl]amino]sulfonyl]benzoate, and methyl 2-[[[[[4,6-bis(difluoromethoxy)-2-pyrimidinyl]amino]carbonyl]amino]sulfonyl]benzoate.

12. The method of claim 11 wherein the compound is selected from the group consisting of 2-chloro-6-(1-fluoroethyl)-N-[[(4-methoxy-6-methyl-1,3,5-triazin-2-yl)amino]carbonyl]benzenesulfonamide, and methyl 2-[[[[[4,6-bis(difluoromethoxy)-2-pyrimidinyl]amino]carbonyl]amino]sulfonyl]benzoate.

13. The method of claim 11 wherein the compound is 2-chloro-6-(1-fluoroethyl)-N-[[(4-methoxy-6-methyl-1,3,5-triazin-2-yl)amino]carbonyl]benzenesulfonamide.

14. The method of claim 11 wherein the compound is methyl 2-[[[[[4,6-bis(difluoromethoxy)-2-pyrimidinyl]amino]carbonyl]amino]sulfonyl]benzoate.

15. A method according to claims 11, 12, 13 or 14 in which the gene is Als1.

16. A method according to claims 11, 12, 13 or 14 in which the gene is Als2.

17. A method according to claims 11, 12, 13 or 14 in which the soybean is W20.

18. A method according to claims 11, 12, 13 or 14 in which the soybean is W4—4.

19. A method according to claims 11, 12, 13 or 14 in which the soybean plant is derived from crosses involving line W20.

20. A method according to claims 11, 12, 13 or 14 in which the soybean is derived from crosses involving line W4—4.

21. A method for controlling the growth of undesirable vegetation which comprises applying to cotton plants selected from 19-51a, 19-58b, 19-58c, 19-94, 19-114a, 19-114b, B6D-4a, 20-10, 20-32, 25-1, 25-2, 25-5 and derivatives thereof an effective amount of a compound which is selected from the group consisting of 2-chloro-6-(1-fluoroethyl)-N-[[(4-methoxy-6-methyl-1,3,5-triazin-2-yl)amino]carbonyl]benzenesulfonamide, 1-methylethyl 3-chloro-2[[[[(4,6-dimethyl-2-pyrimidinyl)amino]carbonyl]amino]sulfonyl]benzoate and methyl 2-[[[[[4,6-bis(difluoromethoxy)-2-pyrimidinyl]amino]carbonyl]amino]sulfonyl]benzoate.

22. The method of claim 21 wherein the compound is selected from the group consisting of 2-chloro-6-(1-fluoroethyl)-N-[[(4-methoxy-6-methyl-1,3,5-triazin-2-yl)amino]carbonyl]benzenesulfonamide, and methyl 2-[[[[[4,6-bis(difluoromethoxy)-2-pyrimidinyl]amino]carbonyl]amino]sulfonyl]benzoate.

23. The method of claim 21 wherein the compound is 2-chloro-6-(1-fluoroethyl)-N-[[(4-methoxy-6-methyl-1,3,5-triazin-2-yl)amino]carbonyl]benzenesulfonamide.

24. The method of claim 21 wherein the compound which is methyl 2-[[[[[4,6-bis(difluoromethoxy)-2-pyrimidinyl]amino]carbonyl]amino]sulfonyl]benzoate.

25. The method according to claims 21, 22, 23 or 24 in which the cotton is 19-51a.

26. The method according to claims 21, 22, 23 or 24 in which the cotton is B6D-4a.

27. The method according to claims 21, 22, 23 or 24 in which the cotton is 20-10.

28. The method according to claims 21, 22, 23 or 24 in which the cotton is 25-2.

29. The method according to claims 21, 22, 23 or 24 in which the cotton is 25-5.

30. The method according to claims 21, 22, 23 or 24 in which the cotton is derived from 19-51a.

31. The method according to claims 21, 22, 23 or 24 in which the cotton is derived from B6D-4a.

32. The method according to claims 21, 22, 23 or 24 in which the cotton is derived from 20-10.

33. The method according to claims 21, 22, 23 or 24 in which the cotton is derived from 25-2.

34. The method according to claims 21, 22, 23 or 24 in which the cotton is derived from 25-5.

* * * * *